(12) United States Patent
Beyer et al.

(10) Patent No.: US 12,127,776 B2
(45) Date of Patent: Oct. 29, 2024

(54) METHOD, DEVICE, AND SYSTEM FOR PREVENTING LATERAL STRESS ON BONE STRUCTURES RESULTING FROM OFF-AXIS FORCES CAUSED BY SCREW DRIVER AND SCREW EXTENDER

(71) Applicant: Neo Medical SA, Villette (CH)

(72) Inventors: Morten Beyer, Rødkærsbro (DK); Vincent Lefauconnier, Brent (CH)

(73) Assignee: NEO MEDICAL SA, Villette (CH)

( * ) Notice: Subject to any disclaimer, the term of this patent is extended or adjusted under 35 U.S.C. 154(b) by 350 days.

(21) Appl. No.: 17/619,713

(22) PCT Filed: Jul. 1, 2020

(86) PCT No.: PCT/IB2020/056216
§ 371 (c)(1),
(2) Date: Dec. 16, 2021

(87) PCT Pub. No.: WO2021/001764
PCT Pub. Date: Jan. 7, 2021

(65) Prior Publication Data
US 2022/0304734 A1     Sep. 29, 2022

(30) Foreign Application Priority Data
Jul. 2, 2019 (WO) ................. PCT/IB2019/055640

(51) Int. Cl.
*A61B 17/88*  (2006.01)
*A61B 17/00*  (2006.01)
*A61B 90/00*  (2016.01)

(52) U.S. Cl.
CPC .. *A61B 17/8886* (2013.01); *A61B 2017/0069* (2013.01); *A61B 2090/061* (2016.02); *A61B 2090/067* (2016.02)

(58) Field of Classification Search
CPC ................. A61B 17/8886; A61B 2090/061
See application file for complete search history.

(56) References Cited

U.S. PATENT DOCUMENTS

| | | | | |
|---|---|---|---|---|
| 898,565 A | * | 9/1908 | Duncan | G01B 3/166 |
| | | | | 33/679.1 |
| 1,243,343 A | * | 10/1917 | Roberts | G01B 3/563 |
| | | | | 33/801 |
| 3,650,393 A | | 3/1972 | Reiss et al. | |

(Continued)

FOREIGN PATENT DOCUMENTS

CN     202446242         9/2012
CN     202497225 U      10/2012
(Continued)

OTHER PUBLICATIONS

International Search Report mailed on Jan. 13, 2021, for Application No. PCT/IB2020/056216.
(Continued)

*Primary Examiner* — Christian A Sevilla
(74) *Attorney, Agent, or Firm* — NIXON & VANDERHYE

(57) ABSTRACT

A bone screw tightening device including a screw driver, the screw driver having along its axis a device for providing for radial bendability and at a same time preserving torsional stiffness along an axis of longitudinal extension of the screw.

9 Claims, 9 Drawing Sheets

(56) References Cited

U.S. PATENT DOCUMENTS

| | | | |
|---|---|---|---|
| 3,740,779 A * | 6/1973 | Rubricuis | A61B 5/1076 606/1 |
| 4,834,757 A | 5/1989 | Brantigan | |
| 5,669,909 A | 9/1997 | Zdeblick et al. | |
| 5,728,098 A | 3/1998 | Sherman et al. | |
| 5,797,918 A * | 8/1998 | McGuire | A61B 17/1714 606/104 |
| 5,913,860 A | 6/1999 | Scholl | |
| 6,113,601 A | 9/2000 | Tatar | |
| 6,368,321 B1 | 4/2002 | Jackson | |
| 6,371,968 B1 | 4/2002 | Kogasaka et al. | |
| 6,423,064 B1 | 7/2002 | Kluger | |
| 6,644,087 B1 | 11/2003 | Ralph et al. | |
| 6,716,214 B1 | 4/2004 | Jackson | |
| 6,743,231 B1 | 6/2004 | Gray et al. | |
| 7,066,937 B2 | 6/2006 | Shluzas | |
| 7,179,225 B2 | 2/2007 | Shluzas et al. | |
| 7,250,052 B2 | 7/2007 | Landry et al. | |
| 7,491,168 B2 | 2/2009 | Raymond et al. | |
| 7,520,879 B2 | 4/2009 | Justis et al. | |
| 7,527,638 B2 | 5/2009 | Anderson et al. | |
| 7,588,575 B2 | 9/2009 | Colleran et al. | |
| 7,604,655 B2 | 10/2009 | Warnick | |
| 7,651,502 B2 | 1/2010 | Jackson | |
| 7,666,189 B2 | 2/2010 | Gerber et al. | |
| 7,691,129 B2 | 4/2010 | Felix | |
| 7,691,132 B2 | 4/2010 | Landry et al. | |
| 7,744,629 B2 | 6/2010 | Hestad et al. | |
| 7,749,232 B2 | 7/2010 | Salerni | |
| 7,811,288 B2 | 10/2010 | Jones et al. | |
| 7,842,044 B2 | 11/2010 | Runco et al. | |
| 7,862,587 B2 | 1/2011 | Jackson | |
| 7,892,238 B2 | 2/2011 | DiPoto et al. | |
| 7,892,259 B2 | 2/2011 | Biedermann et al. | |
| 7,922,725 B2 | 4/2011 | Darst Rice et al. | |
| 7,931,673 B2 | 4/2011 | Hestad et al. | |
| 7,951,172 B2 | 5/2011 | Chao et al. | |
| 7,967,821 B2 | 6/2011 | Sicvol et al. | |
| 8,016,832 B2 | 9/2011 | Vonwiller et al. | |
| 8,016,862 B2 | 9/2011 | Felix et al. | |
| 8,034,086 B2 | 10/2011 | Iott et al. | |
| 8,052,724 B2 | 11/2011 | Jackson | |
| 8,088,163 B1 | 1/2012 | Kleiner | |
| 8,114,085 B2 | 2/2012 | Von Jako | |
| 8,128,667 B2 | 3/2012 | Jackson | |
| 8,137,356 B2 | 3/2012 | Hestad et al. | |
| 8,152,810 B2 | 4/2012 | Jackson | |
| 8,167,911 B2 | 5/2012 | Shluzas et al. | |
| 8,197,519 B2 | 6/2012 | Schlaepfer et al. | |
| 8,246,665 B2 | 8/2012 | Butler et al. | |
| 8,262,662 B2 | 9/2012 | Beardsley et al. | |
| 8,262,704 B2 | 9/2012 | Matthis et al. | |
| 8,317,796 B2 | 11/2012 | Stihl et al. | |
| 8,366,747 B2 | 2/2013 | Shluzas | |
| 8,372,121 B2 | 2/2013 | Capote et al. | |
| 8,382,805 B2 | 2/2013 | Wang et al. | |
| 8,394,109 B2 | 3/2013 | Hutton et al. | |
| 8,465,546 B2 | 6/2013 | Jodaitis et al. | |
| 8,469,960 B2 | 6/2013 | Hutton et al. | |
| 8,562,652 B2 | 10/2013 | Biedermann et al. | |
| 8,603,094 B2 | 12/2013 | Walker et al. | |
| 8,603,145 B2 | 12/2013 | Forton et al. | |
| 8,608,746 B2 | 12/2013 | Kolb et al. | |
| 8,617,218 B2 | 12/2013 | Justis et al. | |
| 8,636,783 B2 | 1/2014 | Crall et al. | |
| 8,870,878 B2 | 10/2014 | Gorek | |
| 9,050,139 B2 | 6/2015 | Jackson | |
| 9,066,758 B2 | 6/2015 | Justis et al. | |
| 9,066,761 B2 | 6/2015 | McBride et al. | |
| 9,101,401 B2 | 8/2015 | Dalton et al. | |
| 9,138,261 B2 | 9/2015 | Di Lauro et al. | |
| 9,204,909 B2 | 12/2015 | Rezach et al. | |
| 9,211,143 B2 | 12/2015 | Barry | |
| 9,211,149 B2 | 12/2015 | Hoefer et al. | |
| 9,326,798 B2 | 5/2016 | Kolb et al. | |
| 9,408,649 B2 | 8/2016 | Felix et al. | |
| 9,492,209 B2 | 11/2016 | Biedermann et al. | |
| 9,526,537 B2 | 12/2016 | Meyer et al. | |
| 9,585,702 B2 | 3/2017 | Hutton et al. | |
| 9,655,653 B2 | 5/2017 | Lindner et al. | |
| 9,707,019 B2 | 7/2017 | Miller et al. | |
| 9,924,982 B2 | 3/2018 | Jackson | |
| 9,962,197 B2 | 5/2018 | Dandaniopoulos et al. | |
| 9,968,378 B1 | 5/2018 | Johnson et al. | |
| 10,058,355 B2 | 8/2018 | Beyer | |
| 2003/0114860 A1 | 6/2003 | Cavagna et al. | |
| 2004/0144149 A1 | 7/2004 | Strippgen et al. | |
| 2005/0131408 A1 | 6/2005 | Sicvol | |
| 2005/0192570 A1 | 9/2005 | Jackson | |
| 2005/0192579 A1 | 9/2005 | Jackson | |
| 2005/0240197 A1 | 10/2005 | Kmiec, Jr. | |
| 2006/0036244 A1 | 2/2006 | Spitler et al. | |
| 2006/0089644 A1 | 4/2006 | Felix | |
| 2006/0111712 A1 | 5/2006 | Jackson | |
| 2006/0111715 A1 | 5/2006 | Jackson | |
| 2006/0217719 A1 | 9/2006 | Albert et al. | |
| 2006/0241599 A1 | 10/2006 | Konieczynski et al. | |
| 2006/0276789 A1 | 12/2006 | Jackson | |
| 2007/0078460 A1 | 4/2007 | Frigg et al. | |
| 2007/0106123 A1 | 5/2007 | Gorek et al. | |
| 2007/0233091 A1 | 10/2007 | Naifeh et al. | |
| 2007/0239159 A1 | 10/2007 | Altarac et al. | |
| 2007/0261868 A1 | 11/2007 | Gross | |
| 2007/0270866 A1 | 11/2007 | Von Jako | |
| 2008/0039839 A1 | 2/2008 | Songer et al. | |
| 2008/0119852 A1 | 5/2008 | Dalton et al. | |
| 2008/0147129 A1 | 6/2008 | Biedermann et al. | |
| 2008/0154279 A1 | 6/2008 | Schumacher et al. | |
| 2008/0200918 A1 | 8/2008 | Spitler et al. | |
| 2008/0243189 A1 | 10/2008 | Purcell et al. | |
| 2008/0262318 A1 | 10/2008 | Gorek et al. | |
| 2008/0294172 A1 | 11/2008 | Baumgart | |
| 2008/0294203 A1 | 11/2008 | Kovach et al. | |
| 2009/0171391 A1 | 7/2009 | Hutton et al. | |
| 2009/0204159 A1 | 8/2009 | Justis et al. | |
| 2009/0221879 A1 | 9/2009 | Gorek | |
| 2009/0222045 A1 | 9/2009 | Gorek | |
| 2009/0281571 A1 | 11/2009 | Weaver et al. | |
| 2010/0152785 A1 | 6/2010 | Forton et al. | |
| 2010/0292742 A1 | 11/2010 | Stad et al. | |
| 2010/0312103 A1 | 12/2010 | Gorek et al. | |
| 2011/0040328 A1 | 2/2011 | Miller et al. | |
| 2011/0106179 A1 | 5/2011 | Prevost et al. | |
| 2011/0166606 A1 | 7/2011 | Stihl et al. | |
| 2011/0172718 A1 | 7/2011 | Felix et al. | |
| 2011/0245883 A1 | 10/2011 | Dall | |
| 2011/0263945 A1 | 10/2011 | Peterson et al. | |
| 2011/0313460 A1 | 12/2011 | McLean et al. | |
| 2011/0319896 A1 | 12/2011 | Papenfuss et al. | |
| 2012/0031792 A1 | 2/2012 | Petit et al. | |
| 2012/0186411 A1 | 7/2012 | Lodahi et al. | |
| 2013/0012999 A1 | 1/2013 | Petit | |
| 2013/0023941 A1 | 1/2013 | Jackson et al. | |
| 2013/0096624 A1 | 4/2013 | Di Lauro et al. | |
| 2014/0031828 A1 | 1/2014 | Patel et al. | |
| 2014/0052187 A1 | 2/2014 | Larry | |
| 2014/0100613 A1 | 4/2014 | Iott et al. | |
| 2014/0128878 A1 | 5/2014 | O'Neil et al. | |
| 2014/0171955 A1 | 6/2014 | Smith | |
| 2014/0277203 A1 | 9/2014 | Atoulikian et al. | |
| 2014/0288655 A1 | 9/2014 | Parry et al. | |
| 2015/0066042 A1 | 3/2015 | Cummins et al. | |
| 2015/0265322 A1 | 9/2015 | Jackson | |
| 2015/0351810 A1 | 12/2015 | Lindner et al. | |
| 2016/0089186 A1 | 3/2016 | Beyer | |
| 2016/0166304 A1 | 6/2016 | Stad et al. | |
| 2016/0287294 A1 | 10/2016 | Kubo et al. | |
| 2016/0346026 A1 | 12/2016 | Bootwala et al. | |
| 2016/0374825 A1 | 12/2016 | Kleiner | |
| 2017/0095272 A1 | 4/2017 | Hutton et al. | |
| 2017/0143384 A1 | 5/2017 | Hutton et al. | |
| 2017/0181774 A1 | 6/2017 | Cahill | |
| 2017/0181775 A1 | 6/2017 | Jackson | |
| 2017/0189082 A1 | 7/2017 | Petit | |

(56) References Cited

U.S. PATENT DOCUMENTS

2017/0348037 A1    12/2017  Sexson et al.
2018/0214186 A1     8/2018  Beyer
2018/0303631 A1*   10/2018  Phan ..................... A61B 17/70

FOREIGN PATENT DOCUMENTS

| CN | 203777040    | 8/2014 |
| CN | 105662662    | 6/2016 |
| FR | 2712521  A1  | 5/1995 |
| TW | M273326  U   | 8/2005 |

OTHER PUBLICATIONS

Written Opinion of the ISA mailed on Jan. 13, 2021, for Application No. PCT/IB2020/056216.

* cited by examiner

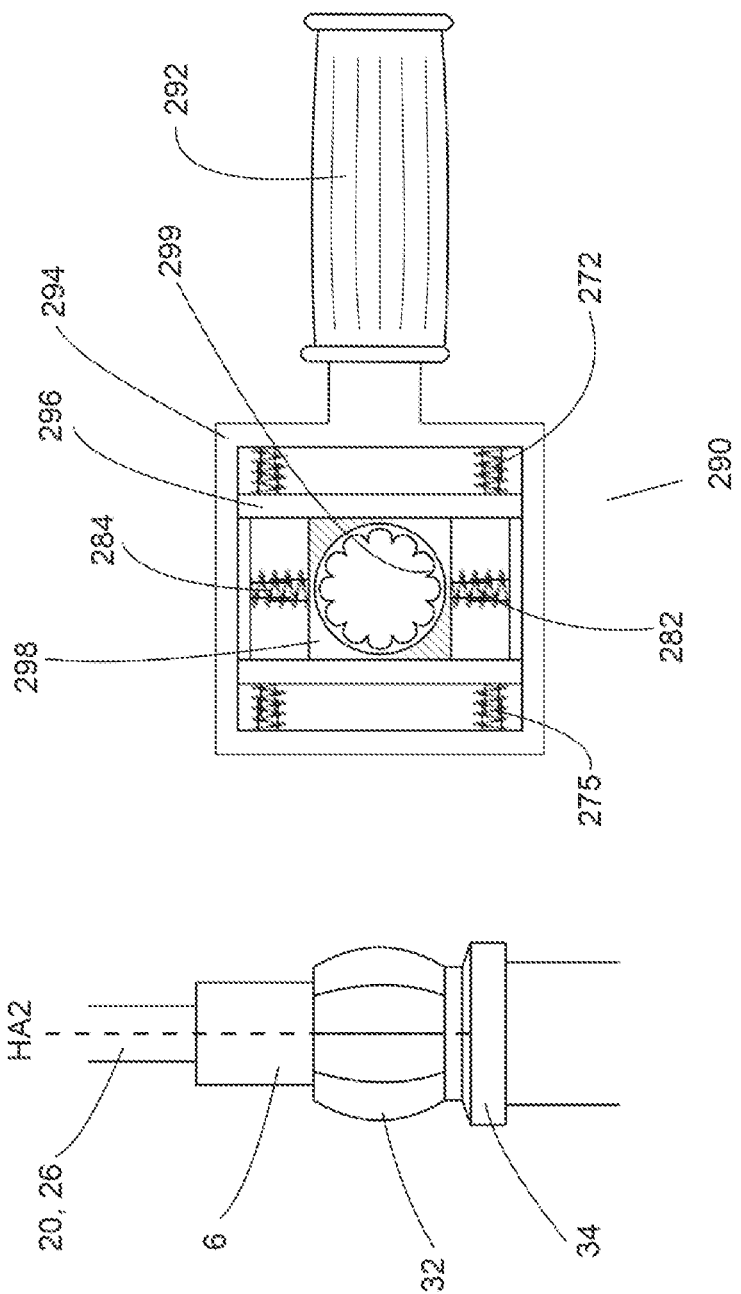

METHOD, DEVICE, AND SYSTEM FOR PREVENTING LATERAL STRESS ON BONE STRUCTURES RESULTING FROM OFF-AXIS FORCES CAUSED BY SCREW DRIVER AND SCREW EXTENDER

CROSS REFERENCE TO RELATED APPLICATIONS

The present patent application is a United States national stage application of International Patent Application No. PCT/IB2020/056216 filed on Jul. 1, 2020 designating the United States, and claims foreign priority to International Patent Application with the Serial No. PCT/IB2019/055640 that was field on Jul. 2, 2019, the contents of both these documents herewith incorporated by reference in their entirety.

FIELD OF THE INVENTION

The present patent application is directed to the field of surgical methods that use bone screws that can be attached to a bone, for example vertebra, and methods, devices, and systems for tightening or fastening a bone screw to a bone.

BACKGROUND

In the field of surgery where a surgeon or operator needs to attach or fasten a bone screw to a bone, for example for securing or fastening a bone, bone fragments, or different bones together, for example via a surgical incision to a living organism, often a first axis defined by an extension of the bone anchor part of the bone screw and a second axis defined by the screw driver of the fastening tool will become misaligned. Ideally, in case the screw head and the bone anchor of the bone screw are monoaxial, the first and the second axis should be maintained in axis with each other. The misalignment is usually the result of the poor view that a surgeon or operator has to the surgical site, or the very limited or non-existing view to the actual axis that the bone anchor has taken inside the bone. The misalignment can force the first axis of the bone anchor of its initially desired positioning and axis, thereby moving the bone out of the initial position. This can lead to problems of parasitic lateral torques, strains or stresses between the bone anchor of screw head, and the bone, that can remain even after a surgery. Also, surgeons tend to apply strong torques to the fastening tool whilst the first axis and the second axis are misaligned, so that the lateral strains are exacerbated.

For example, in the field of orthopedic surgery, U.S. Pat. No. 10,058,355, this reference herewith incorporated by reference in its entirety, describes an orthopedic implant kit that provides for a pedicle screw, a corresponding set screw, a rod, and the tools to operate these, including a screw extender for holding the pedicle screw, and a set screw driver for threadably tightening the set screw relative to screw head of pedicle screw. With this toolkit, it is possible that the threaded part of bone screw is fastened to a bone, e.g. vertebra, and as a connection between screw driver and screw head can be very rigid, any tightening of the bone screw out of the originally-defined first axis will lead to lateral strain that the bone will be subjected too. In addition, while an orientation of the screw head can be given by the orientation of the rod that is placed inside a groove of screw head, and ideally the rod should be arranged perpendicular to the axis defined by the screw head, by misaligning the axis defined by a set screw that is holding the rod inside the groove, for example with the set screw driver, the screw head can be subject to undesired lateral strains that will lead to a strain applied to a bone to which the bone screw is fastened to. These undesired lateral strains can lead to substantial problems post-surgery, and can be felt as chronic pain by the living being post-surgery, and can also lead to improper healing of the bone structures affected by the surgery. The lateral strains can also lead to overloading of implants which can in turn lead to material failures or implant loosening, for example post-surgery.

Therefore, there is a strong need for substantially improved solutions for providing bone tightening systems and orthopedic implant kits to surgeons, physicians, laboratory operators, in light of the above-discussed deficiencies. In addition, there is a strong need for providing tools or devices that can measure an axis of orientation of a bone fastening rod relative to a central axis of a head of a pedicle screw.

SUMMARY

According to one aspect of the present invention, a bone screw tightening device is provided including a screw driver, the screw driver having along its axis a device for providing for radial bendability and at a same time preserving torsional stiffness along an axis of longitudinal extension of the screw.

According to another aspect of the present invention, a device for measuring an angle between an axis of longitudinal extension of a bone fastening rod and an axis of a screw head of a pedicle screw of an orthopedic implant kit is provided, the device including a device configured to be slid over a screw extender of the orthopedic implant kit.

According to still another aspect of the present invention, a device for measuring an angle between an axis of longitudinal extension of a bone fastening rod and an axis of a screw head of a pedicle screw of an orthopedic implant kit is provided, the device preferably configured to be slid over a screw extender of the orthopedic implant kit, the device having two distance measurement sensors opposing each other at a front facing end of the device, the distance measurement sensors configured to measure a distance between the sensors and a position of the rod on each side of the screw head.

BRIEF DESCRIPTION OF THE SEVERAL VIEWS OF THE DRAWINGS

The accompanying drawings, which are incorporated herein and constitute part of this specification, illustrate the presently preferred embodiments of the invention, and together with the general description given above and the detailed description given below, serve to explain features of the invention.

FIGS. 3A to 3C show different embodiments of with different devices associated to a bone fastening system for off-axis prevention, with FIG. 3A showing a schematic and exemplary side view of a bone fastening system, including a screw extender, a screw driver, and a bone screw, the bone screw having a bone anchor and a screw head, and spring-biased handles 25, 29, FIG. 3B showing a top view of an exemplary handle 290 for engaging with screw extender 6, and FIG. 3C shows a top view of an exemplary handle 250 for engaging with screw driver 20, 26;

Herein, identical reference numerals are used, where possible, to designate identical elements that are common to the figures. Also, the images are simplified for illustration purposes and may not be depicted to scale.

DETAILED DESCRIPTION OF THE SEVERAL EMBODIMENTS

Figure 1:
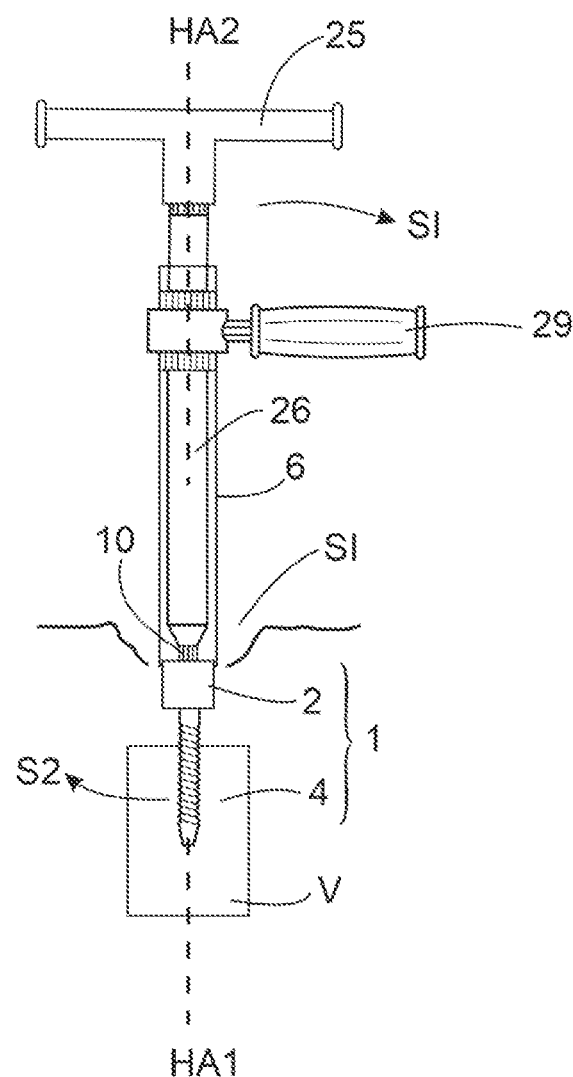
FIG. 1 shows a an exemplary orthopedic bone screw tightening system with screw driver 26, handles 25, 29, engagement element 10 for bone screw 1, and bone screw 1 and bone V, illustrating a potential problem when tightening screw 1 to bone V.

FIG. 1 shows a first representation showing the problem that can be caused by a parasitic strain S2 that is present between bone anchor 4 of bone screw 1, for example when a surgeon or operator tightens screw 1 to bone V, for example via handles 25, 29 and screw driver 26. Specifically, in this variant, bone screw 1 may be a mono-axial screw where head 2 and bone anchor 4 are fixed to each other, and always have the same orientation relative to each other. In this respect, they are oriented along an axis HA1. Next, screw driver 26 is removably engaged with screw head 2 with engagement part 10, and has an axis of longitudinal extension HA2. Screw head 2 is placed inside a surgical incision S1 that allows to access screw head 2. It is possible that operator or surgeon does not retain the axis of screw driver 26 HA2 in axis HA2 of bone screw 1 by an out of axis movement S1. As the connection between screw driver 26 and screw 1, in this variant, does not allow for an angular change between HA1 and HA2, the movement S1 will cause strain S2 between bone anchor 4 of screw 1, or will move bone V from its desired position, out of the orientation defined by axis HA1.

Figure 2:
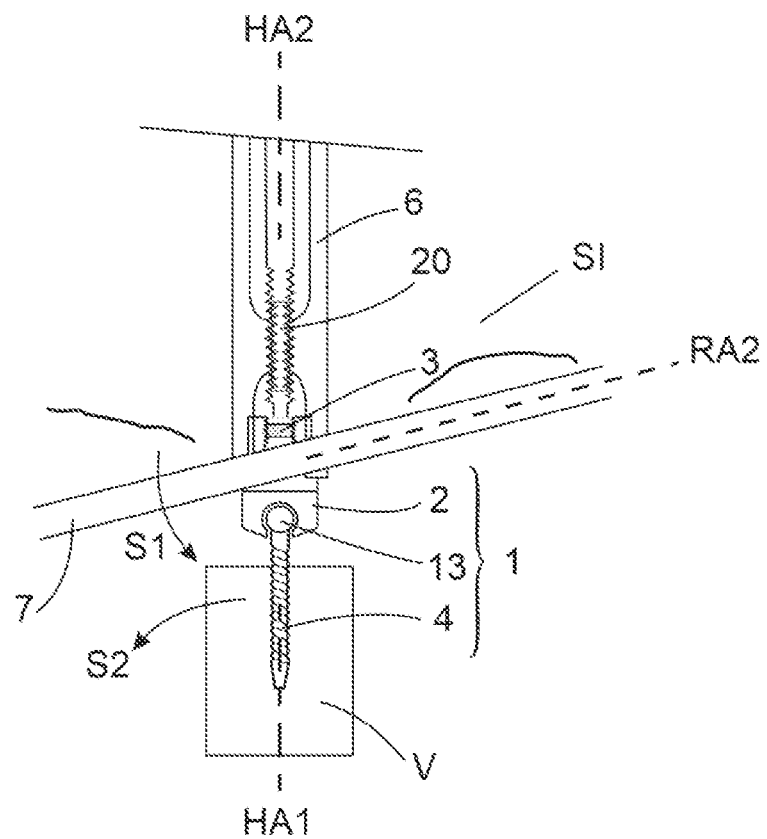
FIG. 2 shows a an exemplary bone screw tightening system with screw driver 20, screw extender 6, fixation rod 7, poly-axial bone screw 1, set screw 3 for holding rod 7 to screw head 2, and vertebra bone V, illustrating another potential problem when tightening screw 1 to bone V.

FIG. 2 shows a second representation showing the problem that can be caused by an operator or surgeon, specific to an orthopedic fixation system, where a pedicle bone screw 1 has already been fixed to a vertebra V by bone anchor 4, for thereafter fixing adjacent vertebrae via pedicle bone screw 1 with a rod 7. The problem can be caused when rod 7 is affixed or tightened to screw head 4 of pedicle screw 1 by a set screw 3 that can threadably engage with head 2, and has a groove for accommodating rod 7. In this situation, the pedicle screw 1 is a poly-axial or multi-axial screw, where head 2 and threaded part or bone anchor 4 can take different angular positions relative to each other, due to joint, engagement, or orientation mechanism 13. In this representation, exemplarily bone anchor 4 and head 2 are shown to be aligned in the same axis, for example HA1 being equal to HA2, but these axes can also be oblique to one another, as a poly-axial screw is used.

For example, inside the surgical incision S1, when tightening set screw 3 to screw head 2, rod 7 having an axis of orientation RA2 can be arranged non-perpendicularly to axis HA2 that is defined mainly by the orientation of screw head 2. Due to the connection between screw head 2 and screw extender 6, and screw driver 20 for set screw 3 via set screw 3, screw driver 20 will have the same axis HA2. Once set screw 3 is tightened, and the axis HA2 and RA2 are not perpendicular to each other, as exemplarily shown in FIG. 2, this can cause strain S1 to screw head 2 that will translate to strain S2 to vertebrae V, as rod 7 will abut against a side of groove of screw head 2, and will not lie properly inside groove. As discussed above, in this variant, screw head 2 may be freely orientable relative to bone anchor 4 with an orientation mechanism 13 thereby forming a poly-axial screw, such that axis HA1 of bone anchor 4 and axis HA2 of screw head 2 may not coincide.

Due to the limited view provided by surgical incision S1 to surgeon or operator, and in some cases the oblique position of axis RA1 rod 7 relative to an extension of the spine, it is possible that screw head 2 and its orientation HA2 cannot be oriented properly relative to rod 7 without additional help, to be ideally arranged perpendicular to RA2. Once set screw 3 is tightened, usually the poly-axiality of pedicle screw 1 is lost, and for this reason screw head 2 may not automatically orient itself perpendicularly to rod 7 simply by tightening set screw 3 to screw head 2 by set screw driver 3. Accordingly, a device, system or method is desired that can measure the orientation of rod 7 relative to screw head 2 during the surgical procedure, so that the surgeon or operator can properly orient screw head 2 to be perpendicular or substantially perpendicular to rod 7, before tightening set screw 3 to head 2, for attachment of rod 7 to pedicle screw 1.

Figure 3A:
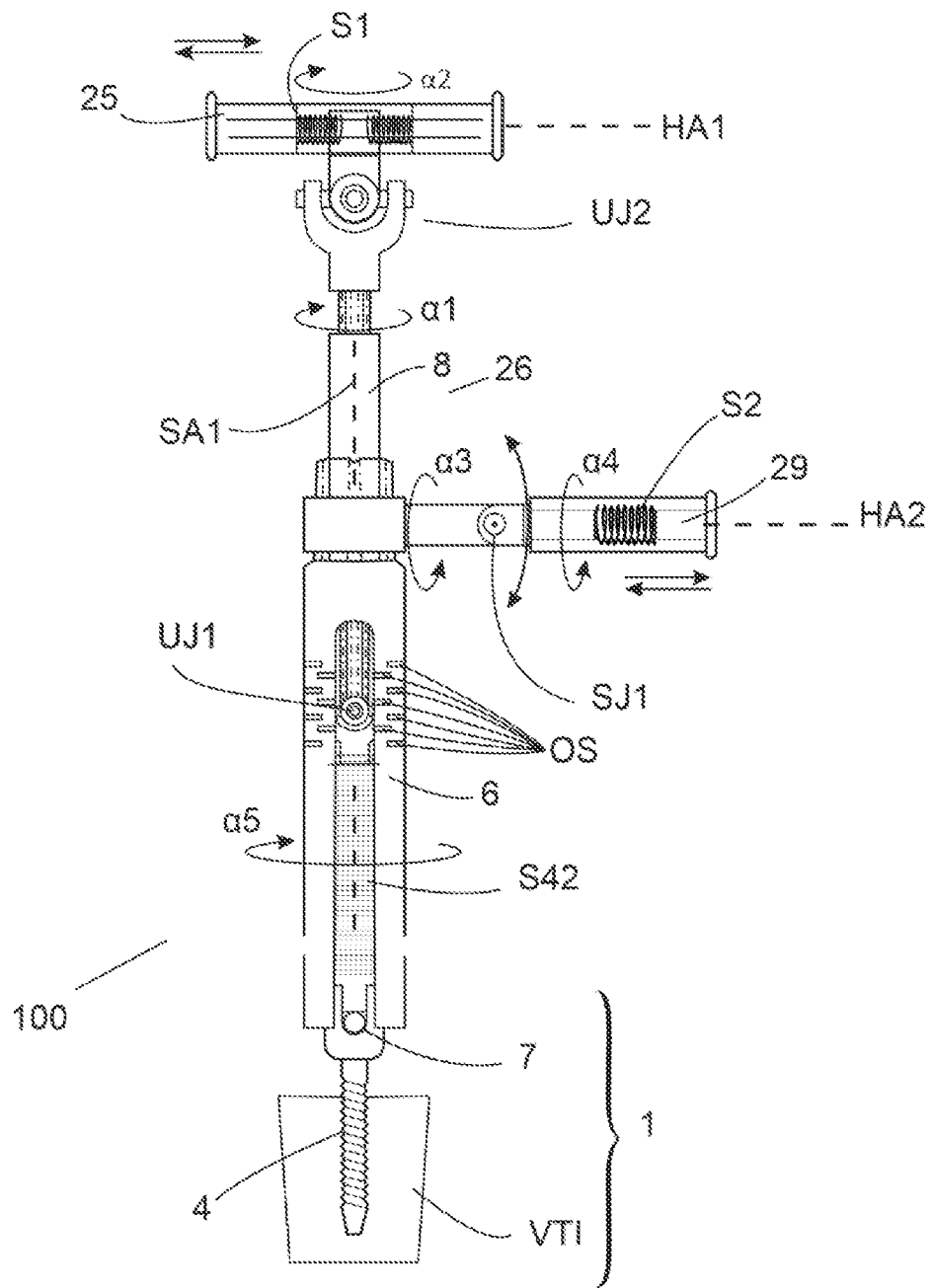
Figure 4:
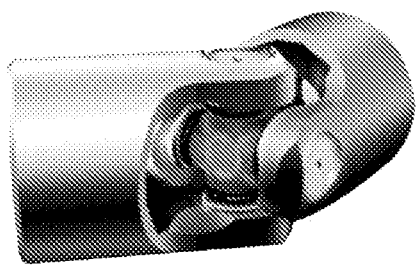
FIG. 4 shows a possible implementation of an universal joint UJ1 and/or UJ2.

According to one aspect of the present invention, as shown in FIG. 3A in a side view and schematic exemplary fashion, a screw driver 26 can be used that has one more universal joints UJ1, UJ2, and a screw extender 6 can be used for removable attachment to a screw head 2 of a bone screw 1. An exemplary universal joint UJ is shown in FIG. 4. This many be a way to limit any parasitic lateral torques to screw head 2 and also to bone anchor 4 (threadbare part) by screw extender 6 and set screw driver assembly 26. The mechanics set up would use two different universal joints (UJ1 and UJ2) and a simple joint (SJ1), as discussed below. The basic principle of operation is that the direction of extension of screw extender 6 (SA2) and the one set screw driver 26 are given by the orientation of screw head 2 (SA3) of pedicle screw 1, and not by forcing the surgeon or operator to change the orientation SA3 manipulating the screw extender 6 and/or set screw driver 26.

An universal joint UJ1 will connected the upper section 8 of the set screw driver 26 with the lower section 20, so that the angular position of lower set screw driver axis SA2 is decoupled from upper set screw driver axis SA1, but by maintaining a fixed angular rotative connection with angles alpha1 and alpha5. FIG. 4 shows an exemplary compact universal joint UJ that could be easily integrated into a screw extender. This feature allows to add bendability to set screw driver 26 or other type of screw driver, whilst preserving a transmission of torque from handles 25, 26 to set screw 3 or other type of bone screw, as the titanium or stainless steel set screw driver 26 is very stiff.

Moreover, in case a screw extender 6 is used, a portion of screw extender 6 below where the handles 25, 29 can be located can also be made less rigid in a direction away from axis SA1 than the remaining part of the screw extender, but by substantially preserving torsional stiffness of screw extender, specially less rigid than the portion of the screw extender that engages with screw head 2 of pedicle screw 1. Specifically, screw extender 6 *a* be made more bendable with respect to an axis SA1, but still preserves a relatively high torsional stiffness to transmit torque. For example, slots or openings OS to screw extender 6 in an area below attachment area of handle 29 can be such that lateral torques off the axis SA1 are much less strong when transmitted via screw extender 6. Screw extender 6 could be made more bendable off the axis SA1 in this area by additional slots or other types of openings OS, the slots being perpendicular to axis SA1, for example as angularly alternating slots, or a softer material at this area could be used. This allows to add additional bendability to the screw extender 6 without impacting its function of guiding rods 7 and set screw driver 26. This area is in an upper part of screw extender 6, and therefore will only minimally impact its operation, i.e. the threadbare engagement between set screw driver 26 and screw extender 6. Moreover, the area with openings OS or other element that provides lateral softness can be such that the lie in a range of the location where universal joint UJ of screw driver 26 will be located, when engaging with set screw 3, or other type of bone screw 1.

A second universal joint UJ2 can be arranged between handle 25 and upper section 8 of screw driver 26. This allows to block rotation of angles alpha1 of upper section 8 of set screw driver 26 to angle of handle 25 (alpha2), but allows for free orientation of handle axis HA1 and upper set screw driver axis SA1. To avoid that the handle 25 can apply to much force through lateral movement, handle 25 can be biased by a biasing spring mechanism S1. This could also be done by a handle that can slip laterally without the biasing spring mechanism S1. This decouples substantially all of the parasitic movement from handle 25 to set screw driver 26 away from axis SA1. An additional biasing mechanism can be also added to cover the other direction, to be perpendicular to axis HA1. Similarly, handle 29 can have a simple joint SJ1 that allows for free up and down pivoting movement of handle 29, but has also a biasing spring mechanism S2 allowing for lateral movements of handle 29 that will be attenuated with less torque to screw extender 6. In a variant, simple joint SJ1 can also be implemented as an universal joint, similar to UJ1 or UJ2.

These elements with handles 25, 29 and set screw driver 26 having universal joint UJ1, and possibly UJ2, the orthopedic pedicle screw tightening system, or other type of bone screw tightening system, is entirely mechanical and can be fully integrated into a toolkit. It is also universally applicable to different types of surgical tools, where an bone anchoring has been made, and could also be used for dental and other applications. It is still possible for the user to apply a parasitic torque, but this set up could strongly reduce such torque, probably by more than 90% as compared to the current solution.

As shown in FIG. 3A, different mechanisms are shown that can be added or implemented to an already existing screw extender/screw driver system, for example but not limited to the one shown in U.S. Pat. No. 10,058,355, that allows to reduce any strain on set screw or bone screw that is not specifically directed to torque that is applied for the tightening of the bone screw by a torque. Specifically, the strains that need to be reduced are the ones that are in any radial direction (360 degrees) away from an axis of longitudinal extension of screw driver/screw extender SA1, or HA21, as the bone screw, see FIGS. 1-3, for example a mono-axial bone screw or a pedicle screw that is not being poly-axial anymore, will translate such lateral movements into a strain to the bone V. For this purpose, the system of FIG. 3 can add flexibly in terms of bendability, that allows to decouple an orientation of the element 10 of screw driver 26 that firmly engages with the bone screw head 2, and the parts that will be handled by the surgeon when tightening the bone screw. Some of these mechanisms are shown as universal joints UJ1 and UJ2 at specific locations, and some of them as springs S1, S2, to provide for a spring-biased suspension to the handles for axes HA1 HA2. Another element is the softening of the screw extender in an upper area, for example with slots or openings OS, at an area where UJ1 is located of the screw driver is located, so that the screw extender can be bent together with the screw driver.

Of course it would be possible to implement the universal joints UJ as simple as possible, for example as elastomeric joints with no moving parts other than the bendable elastomer, or other types of simplified flexible couplings, for example double spring couplings. In this sense, the main function of transferring a tightening torque to the bone screw by preserving or substantially preserving the torsional stiffness of screw driver 26 and screw extender 6 if present, and at the same time providing a decoupling between the main axis of the bone screw and the main axis of the tightening elements is provided, an can be implemented with possible equivalents, such as universal joints, cardan joints, beam couplings, elastomeric couplings, jaw couplings, etc.

FIG. 3B show another variant of a handle 290 that can be used to engage with and hold screw extender 6 at a position relative to pedicle screw 4, for holding screw extender 6. A portion of screw extender 6 is shown with a side view on the left of FIG. 3B. Handle 290 includes a hand grip portion 292 that is configured to be held by the hand of a user, operator, or surgeon, a first frame 294 that is non-movably attached to hand grip portion 294, a second frame 296 that is suspended along a first linear axis relative to first frame 294 by elastic elements 272, 274, in the variant shown the elastic elements 272, 274 being a pair of springs, second frame 296 guided by a linear guiding structure that are located at side parts of first frame 294 and second frame 296, allowing second frame 296 to linearly slide within a certain motional range inside first frame 294, biased by the pairs of elastic elements 272, 274. The linear guiding structure can be implemented as complementary guiding rails, a linear bearing structure, for example with a carriage and guide rail, telescopic slide, or sliding surface for reducing friction between first frame 294 and second frame 296. Moreover, handle 290 further includes a central engagement element 298 for engaging with a corresponding engaging structure 32 of screw extender 6, for example by having a circular opening with circularly-arranged engagement teeth or ridges. Engagement element 298 is elastically biased relative to second frame 296 with two elastic elements, for example but not limited to a coil or leaf spring 282, 284, so that engagement element 298 can slide within a certain motional range relative to second frame 296 along a second linear axis that is substantially perpendicular to first linear axis. Moreover, a linear guiding structure such as but not limited to a complementary rail structure can be provided at side walls of engagement element 298 and side walls of second frame 296, to guide the linear motion along the second linear axis.

With the linear suspension of second frame 296 relative to first frame 294 by an increasing first biasing force with springs 272, 274 for an increased position of second frame 296 off a first central or neutral position, and with the linear suspension of central engagement element 298 relative to second frame 296 by an increasing second biasing force with springs 282, 284 for an increased position of central engagement element 298 off a second central or neutral position, first and second central position corresponding of a location of central axis HA2 when handle 290 is engaging with screw extender 6 in two perpendicularly arranged directions, it is possible to minimize that a user, operator or surgeon urges screw extender off axis that is defined by axis HA1 defined by screw head of pedicle screw 4, and the extension thereof by axis HA2 of screw extender 6 (see FIG. 2).

In addition, engaging structure 32 of screw extender 6 and engaging element 298 of handle 290 are formed such upon their mutual engagement with each other, for example by sliding opening of engagement element 298 of handle 290 to engaging structure, they are configured to be oriented freely within a certain angular range to each other, but still fully lock a rotation of screw extender 6 relative to handle 290 around axis HA2. This can be implemented by an engaging structure 32 having a spherical or ball-like engagement element with engagement ridges or grooves, for example but not limited to a ball hex or ball torx structure, with an at least partially surrounding beveled edge 34 limiting a downward placement of handle 290 to screw extender 6. Edge 34 can be made of a continuous surrounding structure, or by two or more knobs around outer cylindrical surface of screw extender 6. In a variant, it is possible that central engagement element 298 has a curved structure while engaging structure 32 is cylindrically shaped, for allowing a certain range of angular motion of handle 290 relative to axis HA2. This this mechanism between handle 290 and screw extender 6, with engaging structure 32 and central engagement element 298 allows for angular tolerance between handle 290 and screw extender 6 for holding pedicle screw 4, and thereby is functionally equivalent to an universal joint, but also allowing for easy removability.

Figure 3C:
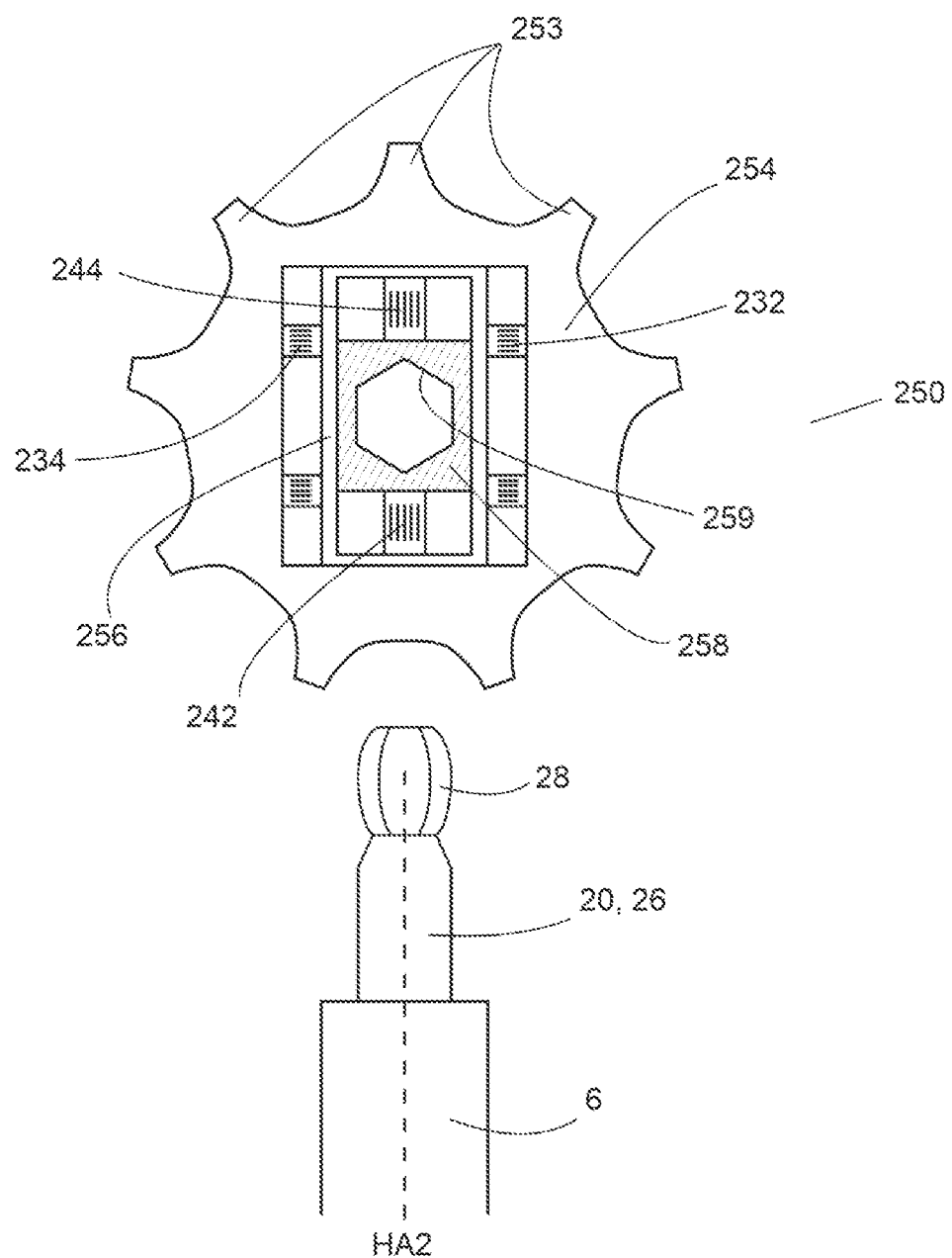

FIG. 3C shows an exemplary embodiment of a handle or knob 250 that can be centrally placed onto an end of screw driver 20, 26, for tightening a pedicle screw 4. For example, handle or knob 250 can be rotated around axis HA2 when in operative connection with screw driver 20, 26, by one hand of user, operator, or surgeon, to turn screw driver 20, 26 relative to screw extender 6, while the other hand can hold screw extender 6 with handle 290. Handle 250 includes an outer ring or holder 254 that can have plurality of knobs or protrusions 253 radially arranged around an outer circumference, or other arrangement to increase a holding friction with a hand of a user, and has an inner rectangularly-shaped opening accommodating a sliding frame 256. Sliding frame 256 is located linearly suspended inside the opening by means of two pairs of elastic elements 232, 234 on each side, for example coil or leaf springs, along for a force-biased linear motional range along a first axis. Sliding frame 256 can be linearly guided by side walls of opening and frame, for example with a corresponding rails structure, or other type of linear bearing structure. Moreover, a central engagement element 258 is located inside a rectangularly shaped opening of sliding frame 256, biased on each side by an elastic element 242, 244, allowing a linear motional range along a second axis that is perpendicular to the first axis.

Central engagement element 258 can have an opening in the shape of a rotary torque tool, for example a hex structure, torx structure, or other type of tool engaging structure for applying a torque to a screw driver 20, 26. For example, central engagement element can be a non-traversing opening having a floor that limits an engagement depth with spherical engagement element 28 of screw driver 20, 26. As shown on the left side of FIG. 3C, an upper end of screw driver 20, 26 is shown, having a spherical engagement element 28 for engaging with central engagement element 258 of handle or knob 259, for example but not limited to a hex ball, hex torx, or other type of tool that allows for an free angular orientation range between handle 250 and screw driver 20, 26, but at the same time allowing for a transmission of a torque around axis HA2 to screw driver 20, 26. In this respect, central engagement element 258 and spherical engagement element 28 have the functional equivalent of an universal joint, but with the possibility of easily removing handle 259 from screw driver 20, 26. It is also possible that handle 250 is equipped with a torque limiting device, for example a breakable pin, or a torque ratchet. In a variant, instead of using helical springs 272, 274, 282, 284, 232, 234, 242, 244, it is possible to use other types of elastic elements, for example but not limited to elastomeric cushions, suspension pistons, elastic cords, leaf spring arrangements, plate springs, volute springs, in both a push or a pull configuration, providing for a force to restore the respective frames or sliders to a neutral position.

Figure 5:
FIG. 5 shows a helix tube, or other type of flexible rod, can be used for one or more portions of screw driver 26, for example at locations of UJ1 and UJ2.

In a variant shown in FIG. 5, a helix tube, or other type of flexible rod, can be used for screw driver 26, or portions thereof, for example at locations of UJ1 and UJ2. This is another device that allows to preserve torsional stiffness around the axis HA2 or SA1, and at the same time allows for bendability off axis HA2 or SA1. Specifically, a double helix tube can be used, with the two helixes running opposite each other that provides strong torsional stiffness.

Figure 6:
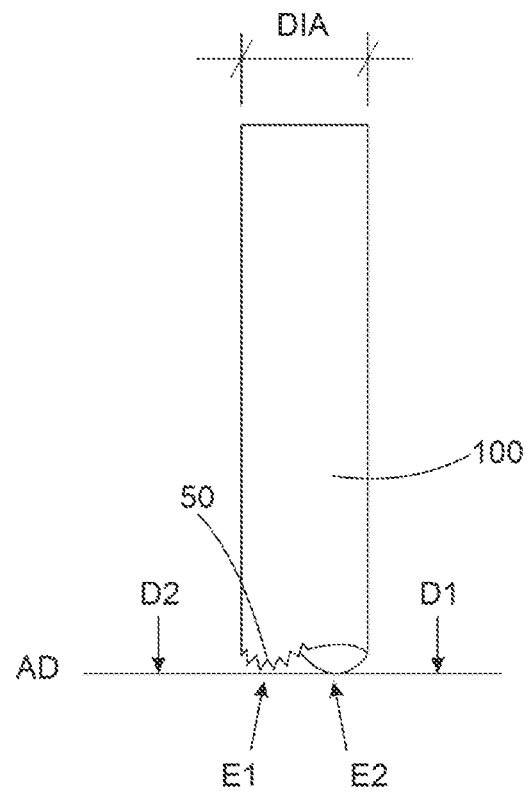
FIGS. 6-8 exemplarily and schematically depict a device 100 that allows to measure and angle between axis HA2 of screw extender 6 and screw head 2, and axis RA2 of rod 7, or determine whether HA2 and RA2 are perpendicular to each other.
Figure 7:
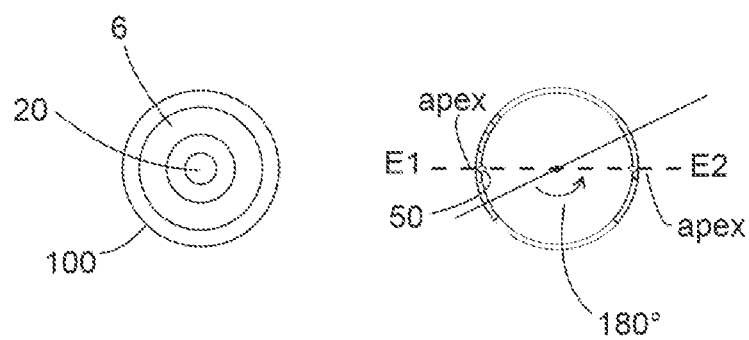
Figure 8:
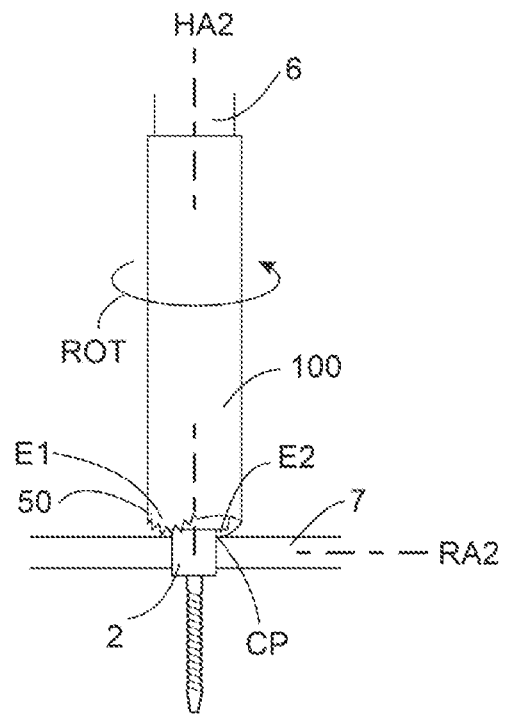

Next, with FIGS. 6 to 8 an exemplary device 100 is described that allows to measure and angle between axis HA2 of screw extender 6 and screw head 2, and axis RA2 of rod 7, or determine whether HA2 and RA2 are perpendicular to each other, so that the surgeon or operator can correct an orientation of screw head 2 relative to rod 7 by moving the screw extender 6. This can be done during the surgery, where bone anchor 4 is already fully attached or fastened to vertebra bone V, and can therefore be done through the surgical incision, by a device 100 that can be slid over the screw extender 6 into the surgical incision.

Basically, as shown in FIG. 6, device 100 is a tubular element that is hollow, for example has a hollow interior cylindrical cavity that has an inner diameter DIA slightly larger than an external diameter of the screw extender 6, so that device 100 can be slid over screw extender 6, for example when none of handles 25, 29 are attached to screw extender 6, as shown in FIG. 8 where device 100 has been slid over the screw extender 6, and shown in FIG. 7 as a cross-sectional view, showing device 100 arranged around screw extender 6, and optionally screw driver 20. Tubular device 100 can have other cross-sectional shapes, for example hexagonal, square, polygonal etc., as long as it is hollow and can be slid over the screw extender 6. At a front face of tubular device 100, the circular front edge includes two protrusions, ridges, or edges E1, E2 arranged at 180° from each other. One protrusion E1 has grooves, is dented, or saw-toothed, or has other type of mechanical irregularities 50 facing from front face, that can generate a vibration to tubular device 100 if the protrusion E1 is slid and pressed against spinal rod 7, while the other protrusion E2 is smooth, so that no vibration occurs when protrusion E2 is slid and pressed against spinal rod 7. Preferably, seen from a center axis of tubular device 100 in a radial direction, protrusion E1 is arranged with grooves 50 in an angular range covering the circular front edge between preferably 90° to just under 180°, more preferably between 90° to 120°. In addition, while the protrusions E1 and E2 are axisymmetric to each other, rotated relative to each other by 180°, the dented protrusion E1 does not protrude as far away from front face of tubular element 100 as the non-dented one E2, for example by a distance difference ΔD. In other words, protrusion distance D1 of dented protrusion E1 is smaller than protrusion distance D2 of non-dented protrusion E1, for example by a difference of 1 mm.

As shown in FIG. 8, operator or surgeon can slide tubular element 100 over screw extender 100, for example after removing or before placing handles 25, 29, and can fully insert tubular element 100 to make sure it touches at least one upper surface of spinal fixation rod 7, at least on one side of screw head 2. This can be done to a screw extender of an orthopedic implant kit as exemplarily shown in U.S. Pat. No. 10,058,355. Thereafter, surgeon or operator can rotate tubular element 100 manually, as indicated by the rotative arrow ROT, for example with his thumb and index finger, pressing tubular element slightly against rod 7. In a first case, where rod 7 is substantially perpendicular to screw head 2, which means axis HA2 is perpendicular to axis RA2, which is the desired orientation of rod 7, the rotation ROT of tubular element 100 relative to screw extender 6 will not cause any vibration, as the teeth 50 are arranged slightly recessed, by a distance difference ΔD, and both protrusions E1 and E2 are asymmetrical tom each other.

However, in a second case where rod 7 is not perpendicular to screw head 2, which means axis HA2 is not perpendicular to axis RA2, which is an undesired orientation of rod 7 relative to head 2, the manual rotation ROT of tubular element will cause teeth 50 to engage on a surface of rod 7, to cause a vibration and possible a ratcheting noise that can be manually sensed and heard by surgeon or operator. This will happen as soon as the relative offset distance of rod 7 on each side of the screw head 2 exceeds the distance difference ΔD, which is caused by the oblique angle that exceeds a certain threshold.

With this device 100, it possible to easily detect, without necessary visual feedback, with a very simple mechanism, whether rod 7 is not arranged perpendicularly to screw head 2, and if surgeon or operator detects the non-perpendicularity, with screw extender 6, screw head 2 can be brought into the desired position by orienting screw extender 6 that is attached to screw head 2, before set screw 2 is tightened, for example before the polyaxiality of pedicle screw 1 is lost or limited.

Figure 9:
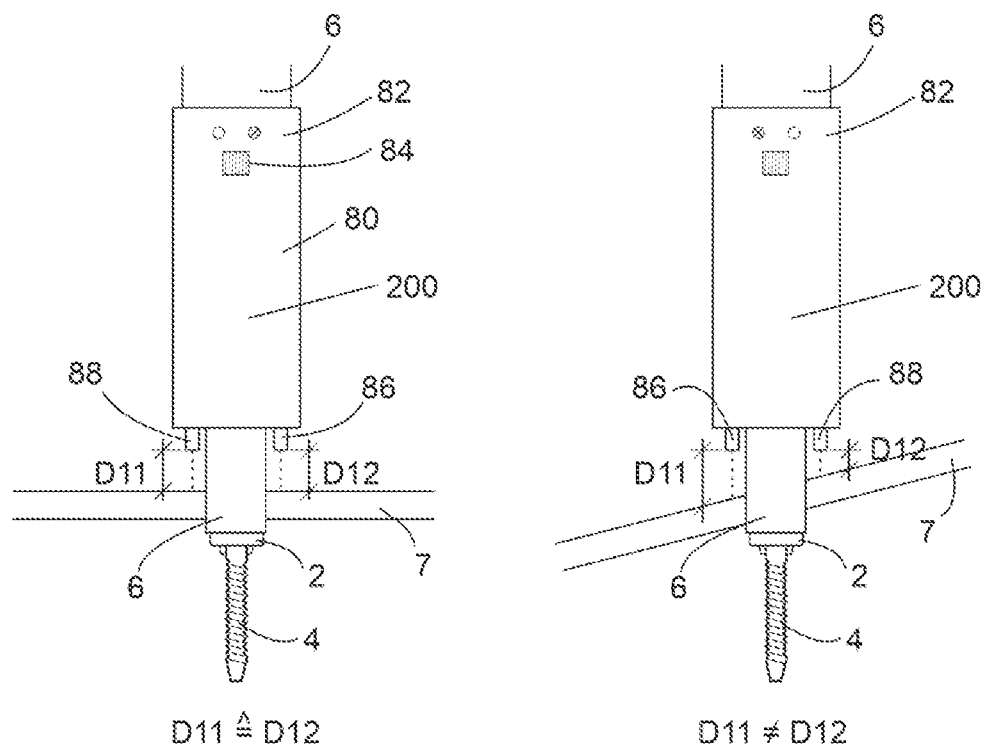
FIGS. 9-10 exemplarily and schematically depict another device 200 that allows to measure and angle between axis HA2 of screw extender 6 and screw head 2, and axis RA2 of rod 7, or determine whether HA2 and RA2 are perpendicular to each other, by an active means.
Figure 10:
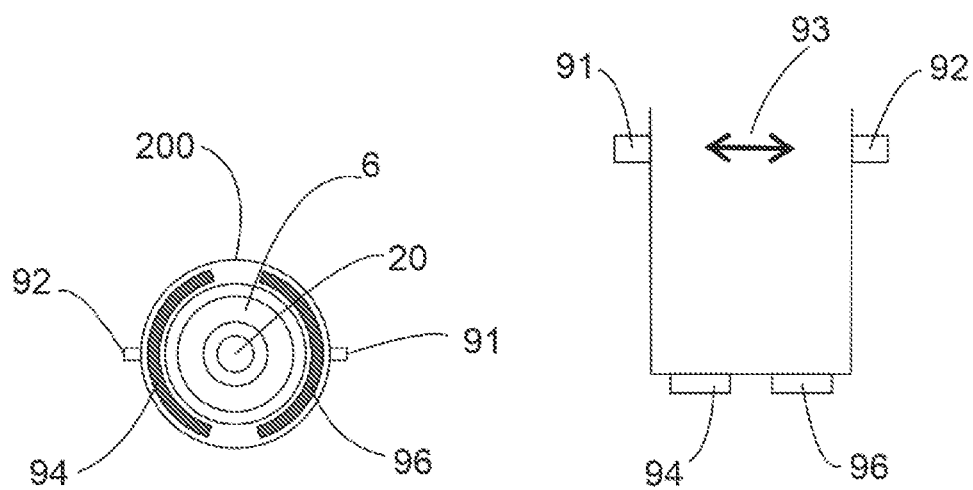

Next, with FIGS. 9-10 another device 200 is described that allows to measure and angle between axis HA2 of screw extender 6 and screw head 2, and axis RA2 of rod 7, or determine whether HA2 and RA2 are perpendicular to each other, so that the surgeon or operator can correct an orientation of screw head 2 relative to rod 7 by moving the screw extender 6. In comparison to device 100, the present device includes electronics and a power supply to measure the distance actively, by the user of distance measurement sensors 86, 88 that are arranged at a front face of device 200, or arranged such that they can measure a distance of the respective sensor 86, 88 to spinal rod 7, on each side of screw head 2 of pedicle screw 1. Sensors 86, 88 can be exemplarily implemented as, but are not limited to, optical, acoustical, ultrasonic, capacitive or inductive distance measurement sensors. FIG. 9 illustrated the device 200 that is placed over screw extender 6 showing, on the left side, rod 7 perpendicularly arranged to screw head 2 (the desired position), and on the right side, rod 7 not perpendicularly arranged to screw head 2. Sensors 88, 86 can measure a distance D11 and D12 on each side of screw head 2, to determine whether the distances are equal, to see if perpendicularity is present. Signals from sensors 86, 88 can be processed by a microcontroller that is powered by a battery, and a result of the comparison of the measured distances D11 and D12 can be indicated to the user for example by optical, acoustical, haptic, or vibratory means, for example via two lights 82 that can show perpendicularity, for example with a green light, or non-perpendicularity, with a red light, for example LED 82. I a variant, the signal can be acoustical, for example with speaker 84 that indicates an acoustic low frequency signal for perpendicularity, and an acoustic high-frequency signal for non-perpendicularity.

With FIG. 10, shows another variant, where detection sensors 94, 96 having a semi-circle contact surface are arranged on each half of the circular front surface of device 200. Moreover, device 200 has an arrow, line or other imprint or indication 93 that shows the desired rotative position of device 200 once placed on screw extender 6, so that device 200 can be approximatively aligned to an axis of longitudinal extension of rod 7, for example along the incision that usually is substantially parallel to rod. Indicator of orientation can also be implemented with small knobs, lump, or protuberances 91, 92 to show orientation of device 200. Front surfaces of detection sensors 94, 96 can detect contact or close proximity to rod 7 on each side of screw head 2, for example by sensors 94, 96 arranged like buttons that can be pressed, or for example by a capacitive measurement to detect close proximity of rod 7.

While the invention has been disclosed with reference to certain preferred embodiments, numerous modifications, alterations, and changes to the described embodiments, and equivalents thereof, are possible without departing from the sphere and scope of the invention. Accordingly, it is intended that the invention not be limited to the described embodiments, and be given the broadest reasonable interpretation in accordance with the language of the appended claims.

The invention claimed is:

1. An orthopedic screw tightening system comprising:
   a screw driver having a screw engagement device and a device for providing for radial bendability and at a same time preserving torsional stiffness along an axis of longitudinal extension of the screw driver; and
   a screw extender for holding a screw and accommodating the screw driver;
   wherein the device of the screw driver includes a helix tube.

2. The orthopedic screw tightening system of claim 1, wherein the screw extender includes an area that is configured to provide for radial bendability and at a same time preserve torsional stiffness along an axis of longitudinal extension of the screw extender.

3. The orthopedic screw tightening system of claim 1, further comprising:
   a first handle configured to engage with the screw extender to manually provide a counter-torque.

4. The orthopedic screw tightening system of claim 3, wherein the first handle is operatively connected to the screw extender via a suspension mechanism configured to suspend the first handle relative to the screw extender.

5. The orthopedic screw tightening system of claim 3, further comprising:
   a second handle configured to engage with the screw driver for applying a torque to the screw.

6. The orthopedic screw tightening system of claim 5, wherein the second handle is operatively connected to the screw driver via a first suspension mechanism configured to suspend the second handle relative to the screw driver.

7. The orthopedic screw tightening system of claim 6, wherein the second handle is operatively connected to the screw driver via a second suspension mechanism, a suspension axis of the first suspension mechanism being perpendicular to a suspension axis of the second suspension mechanism.

8. A device for measuring an angle between an axis of longitudinal extension of a bone fastening rod and an axis of a screw head of a pedicle screw of an orthopedic implant system, the device comprising:
   a tubular element configured to be slid over a screw extender of orthopedic implant system, the tubular element having two frontal protrusions in a direction of an axis of a rotational center of the tubular element, and
   wherein a first protrusion of the two frontal protrusions has a dented front-facing edge, and the second protrusion of the two frontal protrusions protruding farther than the first protrusion in a direction of the axis of the rotational center of the tubular element.

9. A device for measuring an angle between an axis of longitudinal extension of a bone fastening rod and an axis of a screw head of a pedicle screw of an orthopedic implant system, the device comprising:
   a device configured to be slid over a screw extender of the orthopedic implant system, the device having two distance measurement sensors opposing each other at a front facing end of the device, the distance measurement sensors configured to measure a distance between the sensors and a position of the rod on each side of the screw head.

* * * * *